(12) United States Patent
Frasier et al.

(10) Patent No.: US 8,550,995 B2
(45) Date of Patent: *Oct. 8, 2013

(54) SURGICAL ACCESS DEVICES AND METHODS OF MINIMALLY INVASIVE SURGERY

(75) Inventors: William Frasier, Raynham, MA (US); Anne Drzyzga, Raynham, MA (US); Connie Marchek, Raynham, MA (US); Sara Dziedzic, Raynham, MA (US); Holly Brideau, West Roxbury, MA (US); Thomas J Runco, Raynham, MA (US); Nicholas Pavento, Raynham, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/163,258

(22) Filed: Jun. 17, 2011

(65) Prior Publication Data

US 2011/0245621 A1    Oct. 6, 2011

Related U.S. Application Data

(63) Continuation of application No. 11/325,621, filed on Jan. 4, 2006, now Pat. No. 7,981,031.

(51) Int. Cl.
    *A61B 1/32*    (2006.01)
(52) U.S. Cl.
    USPC .......................................................... 600/244
(58) Field of Classification Search
    USPC ................... 600/224, 214, 233, 219; 606/198
    See application file for complete search history.

(56) References Cited

U.S. PATENT DOCUMENTS

| 55,511 A | 12/1865 | Leutz |
|---|---|---|
| 147,867 A | 2/1874 | Schumacher |
| 413,013 A | 10/1889 | Bainbridge |
| 447,761 A | 3/1891 | Clough |
| 458,708 A | 9/1891 | Daily |
| 475,975 A | 5/1892 | Clough |
| 563,236 A | 6/1896 | Penhall |
| 596,399 A | 12/1896 | Fox |
| 605,652 A | 6/1898 | Pitt |
| 761,821 A | 6/1904 | Clark |
| 1,246,340 A | 11/1917 | Smit |

(Continued)

FOREIGN PATENT DOCUMENTS

| EP | 190014 B1 | 3/1994 |
|---|---|---|
| EP | 698374 A3 | 3/1996 |

(Continued)

OTHER PUBLICATIONS

Mayer, H.M. MD., "A New Microsurgical Technique for Minimally Invasive Anterior Lumbar Interbody Fusuon"; Spine; vol. 22(6); 1997; pp. 691-700.

*Primary Examiner* — Kevin T Truong
*Assistant Examiner* — Michael Araj
(74) *Attorney, Agent, or Firm* — David A. Lane, Jr.

(57) ABSTRACT

A surgical access device includes a proximal frame of fixed construction and a plurality of tissue engaging blades connected to the frame. The plurality of tissue engaging blades may include a first blade that is rotatable, independent of other blades, about an axis that is oriented approximately parallel to a plane defined by the proximal frame.

13 Claims, 12 Drawing Sheets

(56) References Cited

U.S. PATENT DOCUMENTS

| | | |
|---|---|---|
| 1,260,604 A | 3/1918 | Verbsky |
| 1,275,520 A | 8/1918 | Bell |
| 1,587,897 A | 6/1926 | Cameron |
| 2,053,868 A | 12/1935 | Grosso |
| 2,320,709 A | 6/1943 | Arnesen |
| 2,532,162 A | 11/1950 | Goss |
| 2,592,190 A | 4/1952 | Rubens |
| 2,693,795 A | 11/1954 | Grieshaber |
| 2,954,025 A | 9/1960 | Grieshaber |
| 3,038,468 A | 6/1962 | Raeuchle |
| 3,129,706 A | 4/1964 | Reynolds, Jr. |
| 3,227,156 A | 1/1966 | Gauthier |
| 3,246,646 A | 4/1966 | Murphy, Jr. |
| 3,384,078 A | 5/1968 | Gauthier |
| 3,436,141 A | 4/1969 | Comte |
| 3,486,505 A | 12/1969 | Morrison |
| 3,522,799 A | 8/1970 | Gauthier |
| 3,563,236 A | 2/1971 | Hansson |
| 3,575,163 A | 4/1971 | Gasper |
| 3,650,266 A | 3/1972 | Pestka et al. |
| 3,716,047 A | 2/1973 | Moore et al. |
| 3,771,518 A | 11/1973 | Greissing |
| 3,807,393 A | 4/1974 | McDonald |
| 3,815,585 A | 6/1974 | Fiore |
| 3,848,601 A | 11/1974 | Ma |
| 3,965,890 A | 6/1976 | Gauthier |
| 4,010,741 A | 3/1977 | Gauthier |
| 4,130,113 A | 12/1978 | Graham |
| 4,156,424 A | 5/1979 | Burgin |
| 4,254,763 A | 3/1981 | McCready |
| 4,263,899 A | 4/1981 | Burgin |
| 4,274,398 A | 6/1981 | Scott, Jr. |
| 4,385,626 A | 5/1983 | Danz |
| 4,421,107 A | 12/1983 | Estes |
| 4,434,791 A | 3/1984 | Darnell |
| 4,545,374 A | 10/1985 | Jacobson |
| 4,562,832 A | 1/1986 | Wilder |
| 4,573,448 A | 3/1986 | Kambin |
| 4,597,382 A | 7/1986 | Perez, Jr. |
| 4,616,635 A | 10/1986 | Caspar et al. |
| 4,686,966 A | 8/1987 | Tsai |
| 4,747,394 A | 5/1988 | Watanabe |
| 4,765,311 A | 8/1988 | Kulik |
| 4,805,984 A | 2/1989 | Cobb, Jr. |
| 4,817,587 A | 4/1989 | Janese |
| 4,862,891 A | 9/1989 | Smith |
| 4,872,451 A | 10/1989 | Moore |
| 4,896,661 A | 1/1990 | Bogert |
| 4,907,132 A | 3/1990 | Parker |
| 4,934,352 A | 6/1990 | Sullivan, Jr. |
| 5,000,163 A | 3/1991 | Ray |
| 5,007,409 A | 4/1991 | Pope |
| 5,052,372 A | 10/1991 | Shapiro |
| 5,052,373 A | 10/1991 | Michelson |
| 5,072,720 A | 12/1991 | Francis et al. |
| 5,125,396 A | 6/1992 | Ray |
| 5,135,525 A | 8/1992 | Biscoping |
| 5,158,543 A | 10/1992 | Lazar |
| 5,171,279 A | 12/1992 | Mathews |
| 5,179,938 A | 1/1993 | Lonky |
| 5,195,505 A | 3/1993 | Josefsen |
| 5,231,973 A | 8/1993 | Dickie |
| 5,231,974 A | 8/1993 | Giglio |
| 5,242,443 A | 9/1993 | Kambin |
| 5,279,567 A | 1/1994 | Ciaglia |
| 5,284,129 A | 2/1994 | Agbodoe |
| 5,292,309 A | 3/1994 | Van Tassel |
| 5,297,538 A | 3/1994 | Daniel |
| 5,304,183 A | 4/1994 | Gourlay |
| 5,312,360 A | 5/1994 | Behl |
| 5,318,010 A | 6/1994 | Lundberg |
| 5,329,938 A | 7/1994 | Lonky |
| 5,342,384 A | 8/1994 | Sugarbaker |
| 5,375,481 A | 12/1994 | Cabrera |
| 5,381,788 A | 1/1995 | Matula et al. |
| 5,382,139 A | 1/1995 | Kawaguchi |
| 5,400,774 A | 3/1995 | Villalta |
| 5,415,666 A | 5/1995 | Gourlay |
| 5,429,121 A | 7/1995 | Gadeli |
| 5,439,464 A | 8/1995 | Shapiro |
| 5,460,165 A | 10/1995 | Mayes |
| 5,472,426 A | 12/1995 | Bonati |
| 5,493,464 A | 2/1996 | Koshikawa |
| 5,499,964 A | 3/1996 | Beck et al. |
| 5,503,617 A | 4/1996 | Jako |
| 5,509,893 A | 4/1996 | Pracas |
| 5,520,610 A | 5/1996 | Giglio |
| 5,554,101 A | 9/1996 | Matula |
| 5,569,248 A | 10/1996 | Mathews |
| 5,616,117 A | 4/1997 | Dinkler |
| 5,667,481 A | 9/1997 | Villalta |
| 5,681,265 A | 10/1997 | Maeda |
| 5,702,177 A | 12/1997 | Lin |
| 5,728,046 A | 3/1998 | Mayer |
| 5,728,097 A | 3/1998 | Mathews |
| 5,746,720 A | 5/1998 | Stouder, Jr. |
| 5,755,660 A | 5/1998 | Tyagi |
| 5,762,629 A | 6/1998 | Kambin |
| 5,769,782 A | 6/1998 | Phan |
| 5,772,582 A | 6/1998 | Huttner et al. |
| 5,772,583 A | 6/1998 | Wright |
| 5,779,629 A | 7/1998 | Hohlen |
| 5,785,648 A | 7/1998 | Min |
| 5,792,044 A | 8/1998 | Foley |
| 5,810,721 A | 9/1998 | Mueller |
| 5,813,978 A | 9/1998 | Jako |
| 5,816,257 A | 10/1998 | Chin |
| 5,827,286 A | 10/1998 | Incavo et al. |
| 5,846,194 A | 12/1998 | Wasson |
| 5,868,668 A | 2/1999 | Weiss |
| 5,873,820 A | 2/1999 | Norell |
| 5,875,782 A | 3/1999 | Ferrari |
| 5,879,291 A | 3/1999 | Kolata |
| 5,882,344 A | 3/1999 | Stouder, Jr. |
| 5,885,210 A | 3/1999 | Cox |
| 5,891,147 A | 4/1999 | Moskovitz |
| 5,893,831 A | 4/1999 | Koros |
| 5,897,490 A | 4/1999 | Fox |
| 5,899,854 A | 5/1999 | Slishman |
| 5,899,901 A | 5/1999 | Middleton |
| 5,902,231 A | 5/1999 | Foley |
| 5,902,233 A | 5/1999 | Farley |
| 5,902,315 A | 5/1999 | DuBois |
| 5,928,139 A | 7/1999 | Koros |
| 5,931,777 A | 8/1999 | Sava |
| 5,944,658 A | 8/1999 | Koros |
| 5,947,896 A | 9/1999 | Sherts |
| 5,951,467 A | 9/1999 | Picha |
| 5,954,635 A | 9/1999 | Foley |
| 5,967,970 A | 10/1999 | Cowan |
| 5,967,972 A | 10/1999 | Santilli |
| 5,967,973 A | 10/1999 | Sherts |
| 5,968,098 A | 10/1999 | Winslow |
| 5,976,146 A | 11/1999 | Ogawa |
| 5,981,147 A | 11/1999 | Hallock |
| 5,984,867 A | 11/1999 | Deckman |
| 6,024,697 A | 2/2000 | Pisarik |
| 6,030,340 A | 2/2000 | Maffei |
| 6,033,406 A | 3/2000 | Mathews |
| 6,042,542 A | 3/2000 | Koros |
| 6,048,309 A | 4/2000 | Flom |
| 6,063,088 A | 5/2000 | Winslow |
| 6,074,343 A | 6/2000 | Nathanson |
| 6,083,154 A | 7/2000 | Liu |
| 6,090,043 A | 7/2000 | Austin et al. |
| 6,090,113 A | 7/2000 | Le Couedic |
| 6,113,535 A | 9/2000 | Fox |
| 6,120,434 A | 9/2000 | Kimura |
| 6,139,493 A | 10/2000 | Koros |
| 6,142,935 A | 11/2000 | Flom |
| 6,152,871 A | 11/2000 | Foley |
| 6,159,179 A | 12/2000 | Simonson |
| 6,162,170 A | 12/2000 | Foley |
| 6,174,282 B1 | 1/2001 | Tan |

| Patent | Date | Name |
|---|---|---|
| 6,176,823 B1 | 1/2001 | Foley |
| 6,176,824 B1 | 1/2001 | Davis |
| 6,187,000 B1 | 2/2001 | Davison |
| 6,196,969 B1 | 3/2001 | Bester |
| 6,197,002 B1 | 3/2001 | Peterson |
| 6,200,263 B1 | 3/2001 | Person |
| 6,200,324 B1 | 3/2001 | Regni, Jr. |
| 6,206,822 B1 | 3/2001 | Foley |
| 6,206,862 B1 | 3/2001 | Giamanco |
| 6,217,509 B1 | 4/2001 | Foley |
| 6,224,545 B1 | 5/2001 | Cocchia |
| 6,224,608 B1 | 5/2001 | Ciccolella |
| 6,241,659 B1 | 6/2001 | Bookwalter |
| 6,261,295 B1 | 7/2001 | Nicholson |
| 6,264,650 B1 | 7/2001 | Hovda |
| 6,267,763 B1 | 7/2001 | Castro |
| 6,277,094 B1 | 8/2001 | Schendel |
| 6,280,379 B1 | 8/2001 | Resnick |
| 6,287,251 B1 | 9/2001 | Tan |
| 6,293,950 B1 | 9/2001 | Lynch |
| 6,306,170 B2 | 10/2001 | Ray |
| 6,322,500 B1 | 11/2001 | Sikora |
| 6,331,157 B2 | 12/2001 | Hancock |
| 6,342,036 B1 | 1/2002 | Cooper |
| 6,371,959 B1 | 4/2002 | Trice |
| 6,371,968 B1 | 4/2002 | Kogasaka |
| 6,394,950 B1 | 5/2002 | Weiss |
| 6,395,007 B1 | 5/2002 | Bhatnagar |
| 6,416,465 B2 | 7/2002 | Brau |
| 6,416,468 B2 | 7/2002 | Deckman |
| 6,427,034 B1 | 7/2002 | Meis |
| 6,428,474 B1 | 8/2002 | Weiss |
| 6,431,025 B1 | 8/2002 | Koros |
| 6,432,049 B1 | 8/2002 | Banta |
| 6,436,033 B2 | 8/2002 | Tan |
| 6,450,952 B1 | 9/2002 | Rioux |
| 6,461,330 B1 | 10/2002 | Miyagi |
| 6,464,634 B1 | 10/2002 | Fraser |
| 6,468,207 B1 | 10/2002 | Fowler, Jr. |
| 6,520,907 B1 | 2/2003 | Foley |
| 6,527,466 B1 | 3/2003 | Blier |
| 6,530,880 B2 | 3/2003 | Pagliuca |
| 6,530,883 B2 | 3/2003 | Bookwalter |
| 6,530,926 B1 | 3/2003 | Davison |
| 6,537,212 B2 | 3/2003 | Sherts |
| 6,591,049 B2 | 7/2003 | Williams |
| 6,592,582 B2 | 7/2003 | Hess |
| 6,593,394 B1 | 7/2003 | Li |
| 6,595,917 B2 | 7/2003 | Nieto |
| 6,599,292 B1 | 7/2003 | Ray |
| 6,616,605 B2 | 9/2003 | Wright |
| 6,639,965 B1 | 10/2003 | Hsieh |
| 6,656,176 B2 | 12/2003 | Hess |
| 6,659,945 B2 | 12/2003 | Ball |
| 6,661,605 B1 | 12/2003 | Pust et al. |
| 6,679,833 B2 | 1/2004 | Smith |
| 6,689,054 B2 | 2/2004 | Furnish |
| 6,692,434 B2 | 2/2004 | Ritland |
| 6,702,741 B2 | 3/2004 | Rioux et al. |
| 6,712,825 B2 | 3/2004 | Aebi |
| 6,716,218 B2 | 4/2004 | Holmes |
| 6,723,043 B2 | 4/2004 | Kleeman |
| 6,729,205 B2 | 5/2004 | Phillips |
| 6,733,445 B2 | 5/2004 | Sherts et al. |
| 6,740,102 B2 | 5/2004 | Hess |
| 6,755,839 B2 | 6/2004 | Van Hoeck |
| 6,764,444 B2 | 7/2004 | Wu |
| 6,793,656 B1 | 9/2004 | Mathews |
| 6,814,700 B1 | 11/2004 | Mueller |
| 6,830,547 B2 | 12/2004 | Weiss |
| 6,869,398 B2 | 3/2005 | Obenchain |
| 6,893,394 B2 | 5/2005 | Douglas |
| 6,896,680 B2 | 5/2005 | Michelson |
| 6,929,606 B2 | 8/2005 | Ritland |
| 6,939,297 B2 | 9/2005 | Gannoe |
| 6,945,933 B2 | 9/2005 | Branch |
| 6,951,538 B2 | 10/2005 | Ritland |
| 6,982,740 B2 | 1/2006 | Adair |
| 7,008,432 B2 | 3/2006 | Schläpfer |
| 7,052,497 B2 | 5/2006 | Sherman |
| 7,074,226 B2 | 7/2006 | Roehm, III |
| 7,081,118 B2 | 7/2006 | Weber |
| 7,087,055 B2 | 8/2006 | Lim |
| 7,097,647 B2 | 8/2006 | Segler |
| 7,141,015 B2 | 11/2006 | Ruane |
| 7,150,714 B2 | 12/2006 | Myles |
| 7,156,085 B2 | 1/2007 | Lewis |
| 7,156,805 B2 | 1/2007 | Thalgott |
| 7,179,225 B2 | 2/2007 | Shluzas |
| 7,179,261 B2 | 2/2007 | Sicvol |
| 7,198,598 B2 | 4/2007 | Smith |
| 7,207,949 B2 | 4/2007 | Miles |
| 7,223,233 B2 | 5/2007 | Branch |
| 7,250,052 B2 | 7/2007 | Landry |
| 7,261,688 B2 | 8/2007 | Smith |
| 7,264,589 B2 | 9/2007 | Sharratt |
| 7,422,596 B2 | 9/2008 | Therin |
| 7,473,222 B2 | 1/2009 | Dewey |
| 7,481,766 B2 | 1/2009 | Lee |
| 7,491,168 B2 | 2/2009 | Raymond |
| 7,491,208 B2 | 2/2009 | Pond et al. |
| 7,513,869 B2 | 4/2009 | Branch |
| 7,524,285 B2 | 4/2009 | Branch |
| 7,556,601 B2 | 7/2009 | Branch |
| 7,758,501 B2 | 7/2010 | Frasier |
| 7,918,792 B2 | 4/2011 | Drzyzga |
| 7,955,257 B2 | 6/2011 | Frasier |
| 7,976,463 B2 | 7/2011 | Dewey |
| 7,981,029 B2 | 7/2011 | Branch |
| 7,981,031 B2 | 7/2011 | Frasier |
| 8,038,611 B2 | 10/2011 | Raymond |
| 2001/0009971 A1 | 7/2001 | Sherts |
| 2001/0029377 A1 | 10/2001 | Aebi |
| 2001/0031969 A1 | 10/2001 | Aebi |
| 2002/0002324 A1 | 1/2002 | McMan |
| 2002/0013514 A1 | 1/2002 | Brau |
| 2002/0022764 A1 | 2/2002 | Smith |
| 2002/0026101 A1 | 2/2002 | Bookwalter |
| 2002/0055670 A1 | 5/2002 | Weiss |
| 2002/0058948 A1 | 5/2002 | Arlettaz |
| 2002/0080248 A1 | 6/2002 | Adair |
| 2002/0095070 A1 | 7/2002 | Furnish |
| 2002/0123754 A1 | 9/2002 | Holmes |
| 2002/0128659 A1 | 9/2002 | Michelson |
| 2002/0143235 A1 | 10/2002 | Pagliuca |
| 2002/0169363 A1 | 11/2002 | Herold |
| 2002/0193666 A1 | 12/2002 | Sherts |
| 2003/0004401 A1 | 1/2003 | Ball |
| 2003/0060687 A1 | 3/2003 | Kleeman |
| 2003/0143941 A1 | 7/2003 | Fujiwara |
| 2003/0149341 A1 | 8/2003 | Clifton |
| 2003/0163030 A1 | 8/2003 | Arriaga |
| 2003/0176772 A1 | 9/2003 | Yang |
| 2003/0191371 A1 | 10/2003 | Smith |
| 2003/0220650 A1 | 11/2003 | Major |
| 2003/0225408 A1 | 12/2003 | Nichols et al. |
| 2004/0002629 A1 | 1/2004 | Branch |
| 2004/0034351 A1 | 2/2004 | Sherman |
| 2004/0039397 A1 | 2/2004 | Weber |
| 2004/0059339 A1 | 3/2004 | Roehm |
| 2004/0087833 A1* | 5/2004 | Bauer et al. .................. 600/201 |
| 2004/0138662 A1 | 7/2004 | Landry |
| 2004/0141302 A1 | 7/2004 | Koch |
| 2004/0141336 A1 | 7/2004 | West |
| 2004/0143167 A1 | 7/2004 | Branch |
| 2004/0143169 A1 | 7/2004 | Branch |
| 2004/0230191 A1 | 11/2004 | Frey |
| 2004/0242969 A1 | 12/2004 | Sherts |
| 2005/0015096 A1 | 1/2005 | Oliver |
| 2005/0043592 A1 | 2/2005 | Boyd |
| 2005/0080320 A1 | 4/2005 | Lee |
| 2005/0131422 A1 | 6/2005 | Anderson |
| 2005/0137461 A1* | 6/2005 | Marchek et al. .............. 600/220 |
| 2005/0159650 A1 | 7/2005 | Raymond |
| 2005/0159651 A1 | 7/2005 | Raymond |
| 2005/0171551 A1 | 8/2005 | Sukovich |
| 2005/0215866 A1* | 9/2005 | Kim ........................... 600/233 |
| 2005/0243592 A1 | 11/2005 | Rust et al. |

| | | |
|---|---|---|
| 2005/0267336 A1 | 12/2005 | Bertolero |
| 2005/0273133 A1 | 12/2005 | Shluzas |
| 2006/0004401 A1 | 1/2006 | Abernathie |
| 2006/0069315 A1 | 3/2006 | Miles |
| 2006/0074278 A1* | 4/2006 | Petit et al. .................. 600/224 |
| 2006/0084844 A1 | 4/2006 | Nehls |
| 2006/0195017 A1 | 8/2006 | Shluzas |
| 2006/0207612 A1 | 9/2006 | Jackson |
| 2006/0224044 A1 | 10/2006 | Marchek |
| 2006/0247651 A1 | 11/2006 | Roehm |
| 2006/0285339 A1 | 12/2006 | Frasier |
| 2007/0038033 A1* | 2/2007 | Jones et al. .................. 600/219 |
| 2007/0060794 A1 | 3/2007 | Efinger |
| 2007/0060795 A1 | 3/2007 | Vayser |
| 2007/0100212 A1 | 5/2007 | Pimenta |
| 2007/0106123 A1 | 5/2007 | Gorek |
| 2007/0118022 A1 | 5/2007 | Hutton |
| 2007/0156023 A1 | 7/2007 | Frasier |
| 2007/0156024 A1 | 7/2007 | Frasier |
| 2007/0156025 A1 | 7/2007 | Marchek |
| 2007/0156026 A1 | 7/2007 | Frasier |
| 2007/0208227 A1 | 9/2007 | Smith |
| 2007/0208228 A1 | 9/2007 | Pavento |
| 2008/0021285 A1 | 1/2008 | Drzyzga |
| 2008/0097164 A1 | 4/2008 | Miles |
| 2009/0015879 A1 | 1/2009 | Nose |
| 2009/0018399 A1 | 1/2009 | Martinelli |
| 2009/0018400 A1 | 1/2009 | Raymond |
| 2009/0203967 A1 | 8/2009 | Branch |
| 2011/0004067 A1 | 1/2011 | Marchek et al. |
| 2011/0213207 A1 | 9/2011 | Frasier |
| 2011/0245621 A1 | 10/2011 | Frasier |
| 2011/0313256 A1 | 12/2011 | Raymond |

FOREIGN PATENT DOCUMENTS

| | | |
|---|---|---|
| EP | 428567 B1 | 5/1996 |
| EP | 1090586 A3 | 10/2001 |
| EP | 1195141 A3 | 1/2004 |
| EP | 908140 B1 | 2/2004 |
| EP | 931509 B1 | 4/2005 |
| EP | 1727477 A1 | 12/2006 |
| EP | 1090589 B1 | 2/2007 |
| EP | 1512367 B1 | 11/2007 |
| EP | 1192905 B1 | 11/2010 |
| EP | 1659928 A4 | 4/2011 |
| FR | 2807313 A1 | 10/2001 |
| GB | 1206277 A | 9/1970 |
| JP | 2198764 A | 8/1990 |
| JP | 10014927 A | 1/1998 |
| WO | WO 9001298 A1 | 2/1990 |
| WO | WO 9221279 A1 | 12/1992 |
| WO | WO 9320741 A1 | 10/1993 |
| WO | WO 9602195 A1 | 2/1996 |
| WO | WO 9628083 A1 | 9/1996 |
| WO | WO 9811818 A1 | 3/1998 |
| WO | WO 9812961 A1 | 4/1998 |
| WO | WO 9817208 A3 | 12/1998 |
| WO | WO 9912466 A1 | 3/1999 |
| WO | WO 9953829 A1 | 10/1999 |
| WO | WO 0018306 A1 | 4/2000 |
| WO | WO 0180725 A1 | 11/2001 |
| WO | WO 02060330 A1 | 8/2002 |
| WO | WO 03000140 A1 | 1/2003 |
| WO | WO 2004000140 A1 | 12/2003 |
| WO | WO 2005096735 A9 | 8/2006 |

* cited by examiner

SURGICAL ACCESS DEVICES AND METHODS OF MINIMALLY INVASIVE SURGERY

REFERENCE TO RELATED APPLICATIONS

This application is a continuation of U.S. patent application Ser. No. 11/325,621, filed Jan. 4, 2006, which is hereby incorporated herein by reference.

BACKGROUND

In surgical procedures, it is important to minimize trauma to the patient and damage to tissue to facilitate patient recovery. One way to accomplish this is to minimize the size of the incision for the surgical procedure and minimize the cutting of tissue to access the target anatomy. A number of retractors are available that are designed to expand a small surgical incision and provide access to a surgical site. Such retractors typically include two or more retractor blades that separate to expand the incision and create an access channel through which to conduct the surgical procedure. One problem with such retractors is that the access channel of the expanded retractor is often restricted to one shape or configuration.

SUMMARY

Disclosed herein are surgical access devices and methods of minimally invasive surgery that minimize tissue trauma and facilitate access to a surgical site. In one exemplary embodiment, a surgical access device may comprise a proximal frame of fixed construction and a plurality of tissue engaging blades connected to the frame. The plurality of tissue engaging blades may include a first blade that is rotatable, independent of other blades, about an axis that is oriented approximately parallel to a plane defined by the proximal frame.

In accordance with another exemplary embodiment, a surgical access device may comprise a proximal frame of fixed construction, a first blade rotatably connected to the proximal frame and rotatable about a first axis that is oriented approximately parallel to a plane defined by the bottom surface of the proximal frame, a second blade rotatably connected to the proximal frame and rotatable about a second axis that is oriented approximately parallel to a plane defined by the bottom surface of the proximal frame, a third blade rotatably connected to the proximal frame and rotatable about a third axis that is oriented approximately parallel to a plane defined by the bottom surface of the proximal frame, and a fourth blade rotatably connected to the proximal frame and rotatable about a fourth axis that is oriented approximately parallel to a plane defined by the bottom surface of the proximal frame. In the exemplary embodiment, the second blade may be positioned opposite the first blade, the third blade may be positioned between the first blade and the second blade, and the fourth blade being positioned opposite the third blade.

In accordance with another exemplary embodiment, a method of providing minimally invasive access to spinal anatomy may comprise making an incision and inserting a plurality of blades of a surgical access device through the incision. The surgical access device may comprise a proximal frame of fixed construction and the plurality of blades may be connected to the proximal frame. The exemplary method may further include advancing the distal ends of the plurality blades into proximity to the spinal anatomy with the blades in a closed configuration in which the blades contact each other to form a continuous enclosed access channel between the frame and the distal ends of the blades. The exemplary method may also include rotating a first one of the blades independent of the other blades about a rotation axis that is oriented approximately parallel to an axis defined by the proximal frame to expand the access channel.

BRIEF DESCRIPTION OF THE FIGURES

These and other features and advantages of the devices and methods disclosed herein will be more fully understood by reference to the following detailed description in conjunction with the attached drawings in which like reference numerals refer to like elements through the different views. The drawings illustrate principles of the devices and methods disclosed herein and, although not to scale, show relative dimensions.

DETAIL DESCRIPTION OF EXEMPLARY EMBODIMENTS

Figure 1:
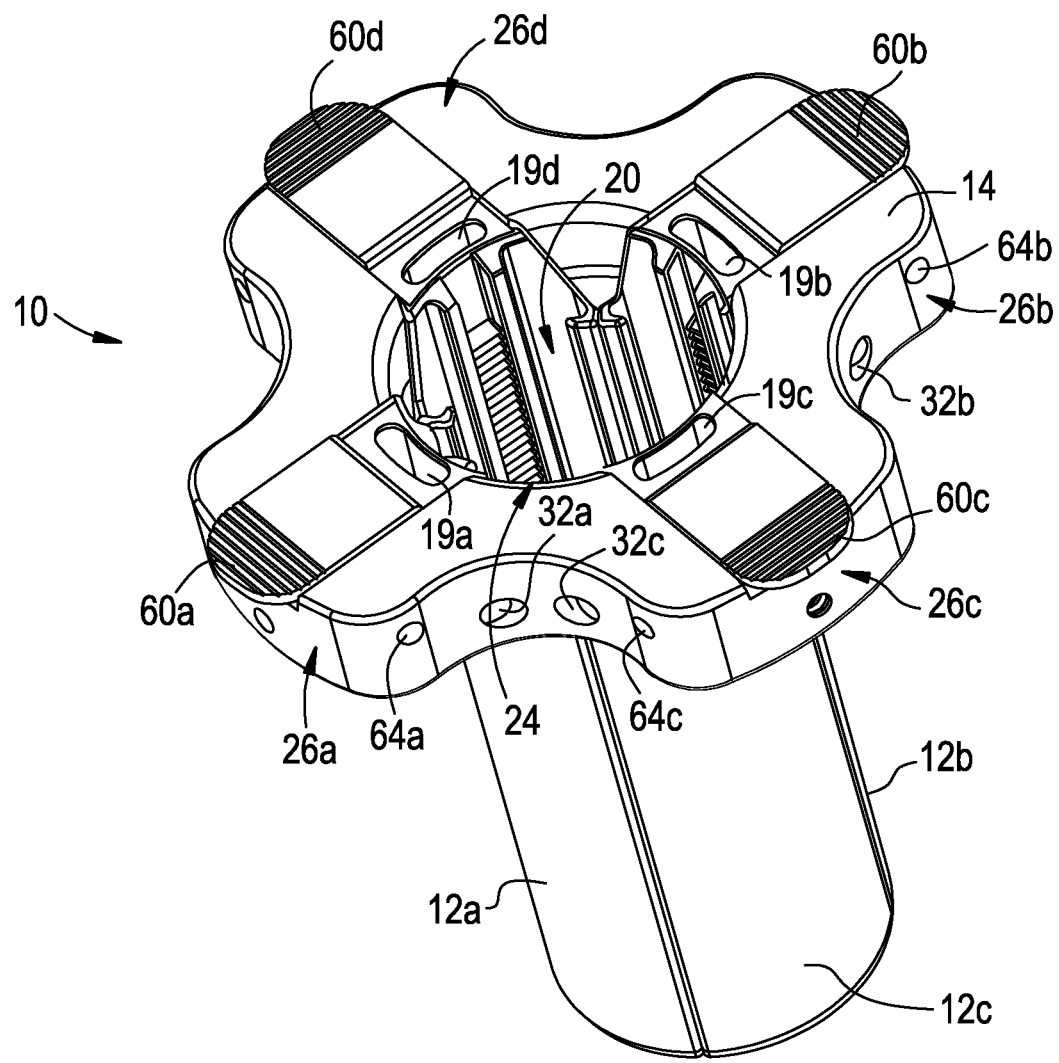
FIG. 1 is a perspective view of an exemplary embodiment of a surgical access device, illustrating the device in a closed configuration.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-5 illustrate an exemplary embodiment of a surgical access device 10 suitable for providing a selectively expandable access channel through which a surgical procedure may be performed on target anatomy. The exemplary surgical access device is particularly suited for minimally invasive spine surgery and, to this end, may be inserted through a relatively small incision to provide a selectively expandable access channel from the skin to the target spinal anatomy. As discussed in more detail below, the exemplary surgical access device 10 includes a plurality of tissue engaging blades 12, some or all of which may be independently rotated to allow the access channel of the surgical access device 10 to be selectively expanded into a variety of different shapes and sizes.

The surgical access device 10 may include a plurality of tissue engaging blades 12. Any number of blades 12 may be provided. In the exemplary, illustrated embodiment, the surgical access device 10 includes four tissue engaging blades: first blade 12a, second blade 12b, third blade 12c, and fourth blade 12d. The first blade 12a is positioned opposite the second blade 12b and is interposed between the third blade 12c and the fourth blade 12d. In the illustrated exemplary embodiment, each blade 12 is analogous in size and shape and may include a proximal end 18 that is configured to facilitate connection of the blade 12 to the surgical access device 10. The proximal end 18 of the blades 12 may include a slot 19 for receiving an instrument employed to rotate the blade 12. In alternative embodiments, a surgical access device may include a plurality of differently configured blades.

The exemplary surgical access device 10 further includes a frame 14 located at the proximal end of the surgical access device 10. The frame 14, in the exemplary embodiment, is generally clover-shaped having a central opening 24 that provide access to an access channel 20 defined by the blades 12 of the surgical access device 10. The frame 14 may include a plurality of the connection nodes 26 to facilitate connection of the blades 12 to the frame 14. In the exemplary embodiment, the frame 14 includes connection nodes 26a-d for connecting the blades 12a-d, respectively, to the frame 14. The plurality of blades 12a-d may be directly connected to the frame 14 through the connection nodes 26a-d, as in the exemplary embodiment, or, in other embodiments, may be indirectly connected to the frame 14. In the exemplary embodiment, the frame 14 has a fixed construction e.g., the frame 14 is fixed in size and shape and, thus, does not expand in use. Rather, one or more of the blades 12a-d may be movable to allow the access channel 20 defined by the blades 12 of the surgical access device 14 to be selectively expanded. The frame 14 may be unitary in construction or may constructed from multiple components. The frame 14 includes a generally planar bottom surface 16 for engaging the surface of the skin about an incision when the surgical access device 10 is in use.

One or more of the blades 12 may be rotatably connected to the frame 14 such that the blade may rotate relative to the frame 14 to expand the access channel 20. In the illustrated exemplary embodiment, first blade 12a, second blade 12b, third blade 12c, and fourth blade 12d may each be rotatably connected to a respective connection node 26a-d of the frame 14 and each may be rotated relative to the frame 14 independent of the other blades. In particular, each blade 12a-d may be connected to a respective connection node 26a-d of the frame 14 by a shaft 30a-d that defines a rotation axis about which the blade 12 rotates relative to the frame 14. At each node 26, a shaft 30 may be positioned across the node 26 through openings 32 in the frame 14 and the shaft 30 may pass through an opening 34 provided through the proximal end 18 of the respective blade 12. In the exemplary embodiment, each shaft 30a-d defines a rotation axis for a respective blade 12a-d and each rotation axis is oriented approximately parallel to the plane defined by the bottom surface 16 of the frame 14. Each shaft 30a-d may be positioned in a common plane, as in the illustrated exemplary embodiment, or may be positioned in separate planes.

Figure 2:
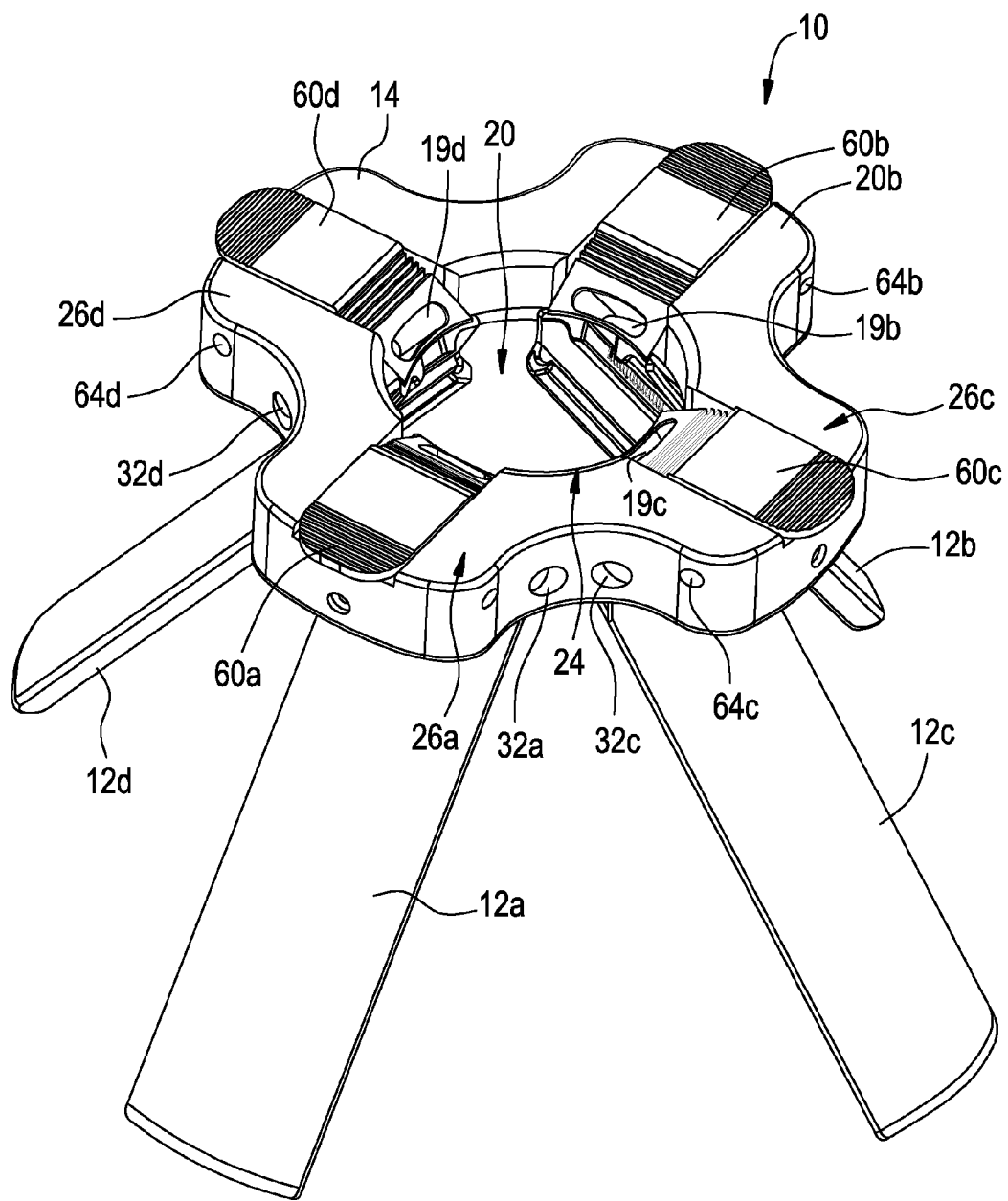
FIG. 2 is perspective view of the surgical access device of FIG. 1, illustrating the device in an expanded configuration.
Figure 3:
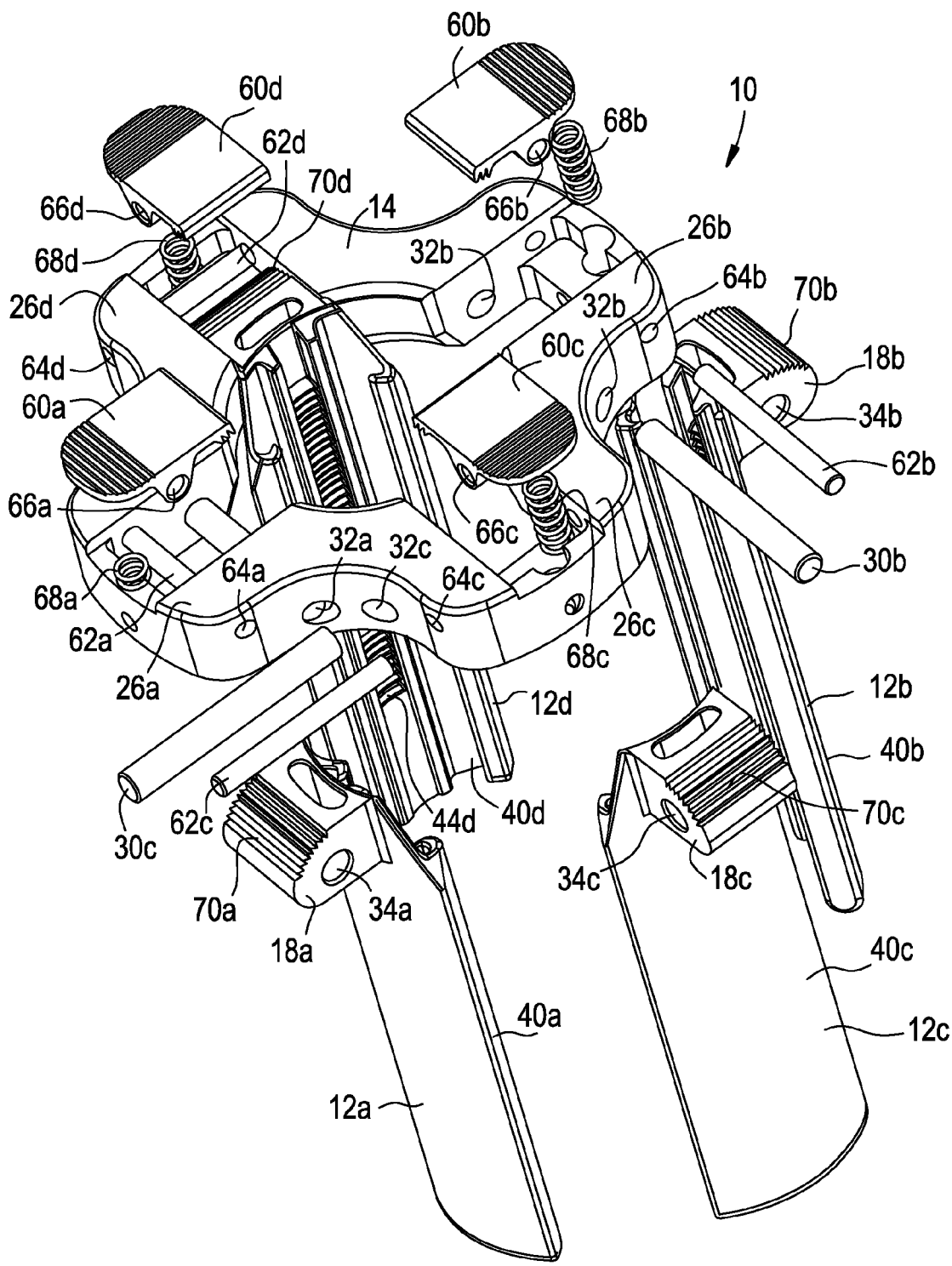
FIG. 3 is an exploded view of the surgical access device of FIG. 1.
Figure 4:
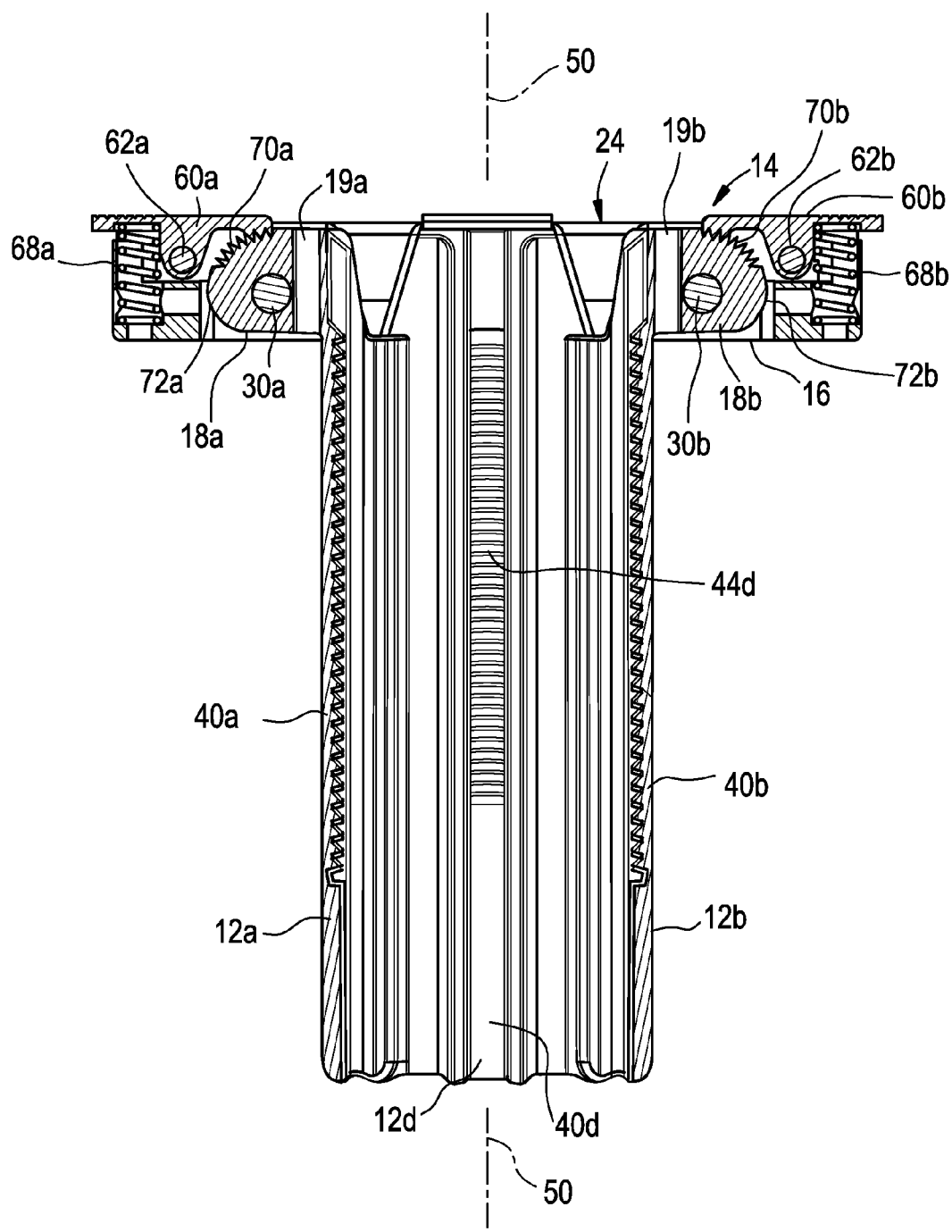
FIG. 4 is a side view in cross section of the surgical access device of FIG. 1, illustrating the device in a closed configuration.
Figure 5:
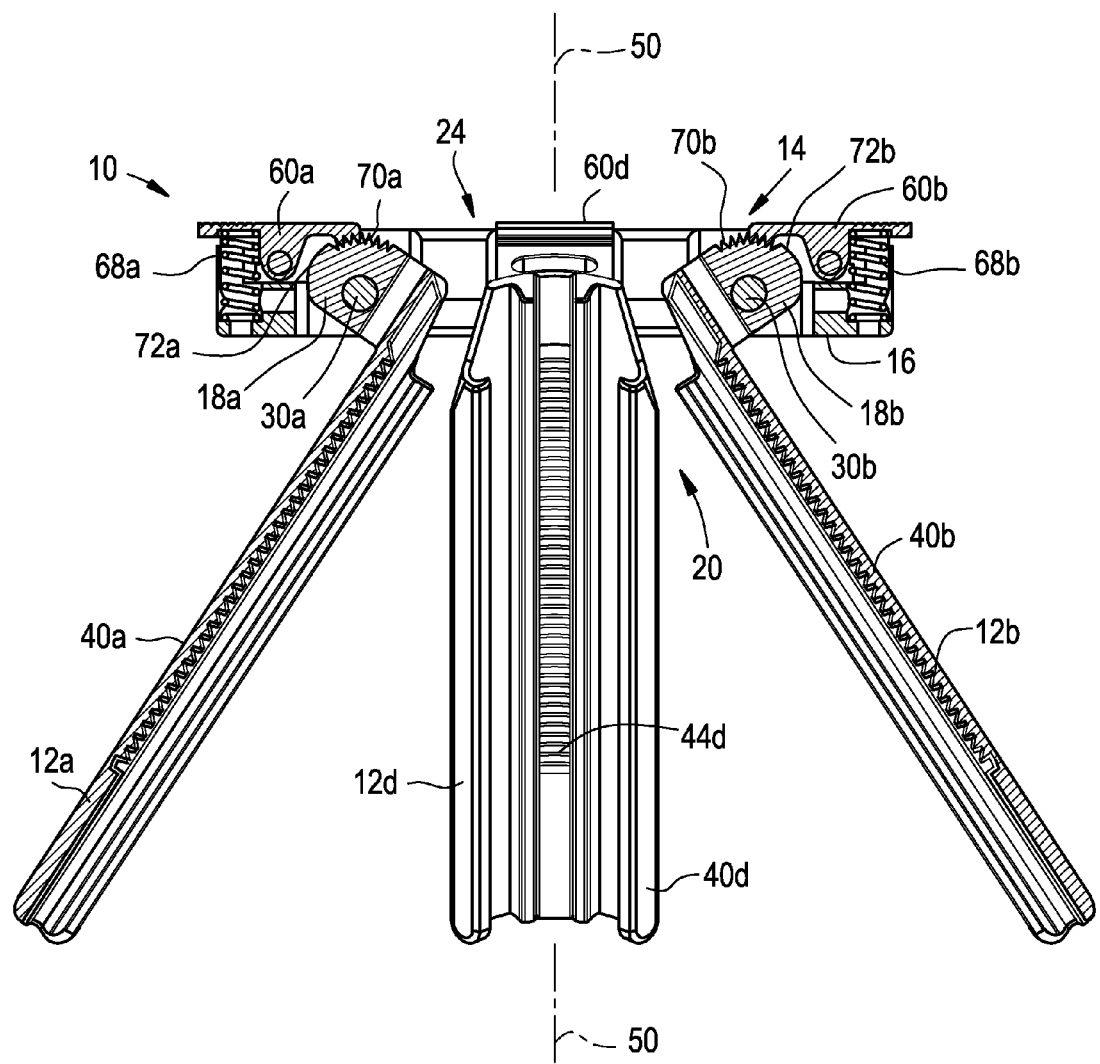
FIG. 5 is a side view in cross section of the surgical access device of FIG. 1, illustrating the device in an expanded configuration.
Figure 6:
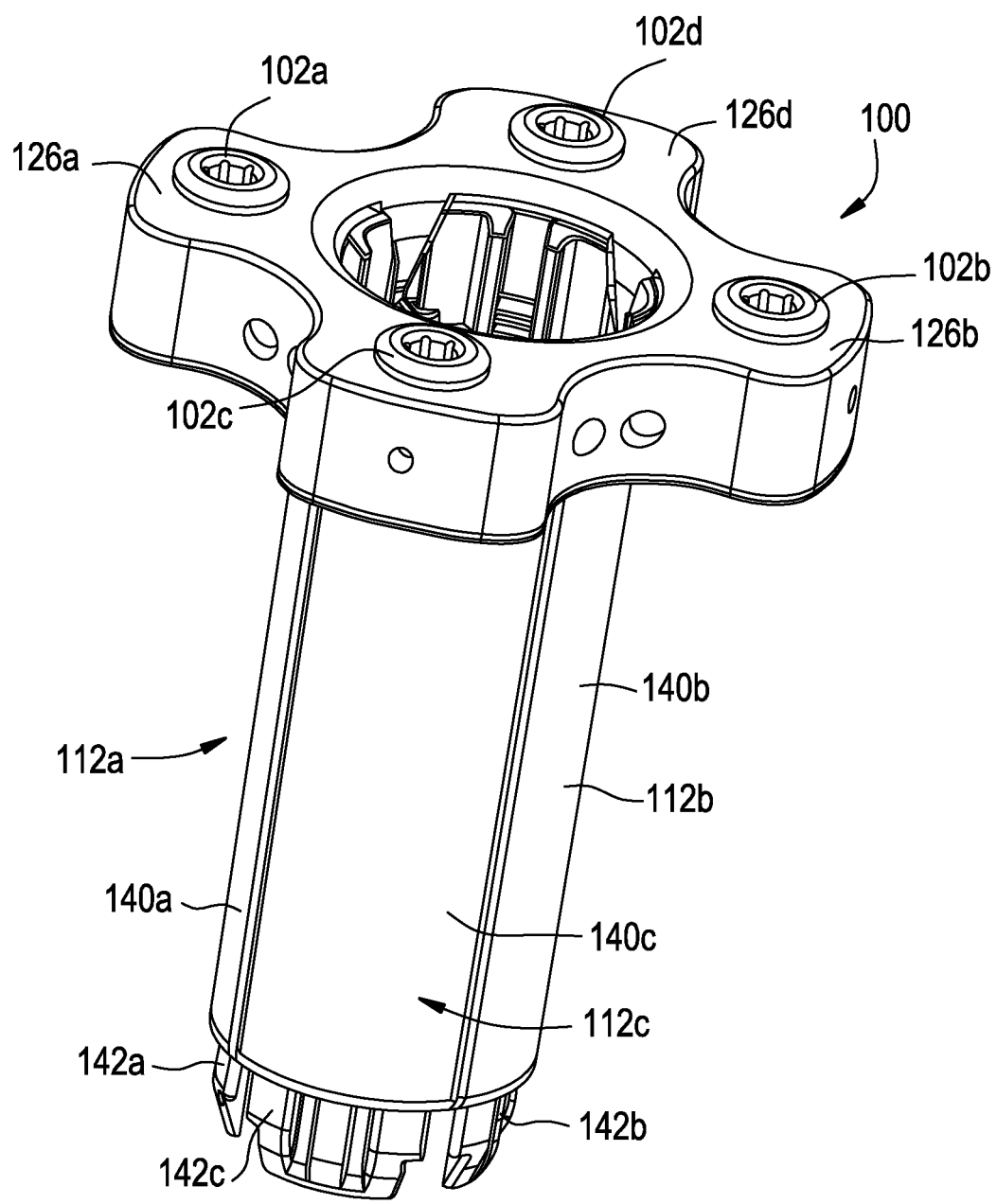
FIG. 6 is a perspective view of another exemplary embodiment of a surgical access device, illustrating the device in a closed configuration.
Figure 7:
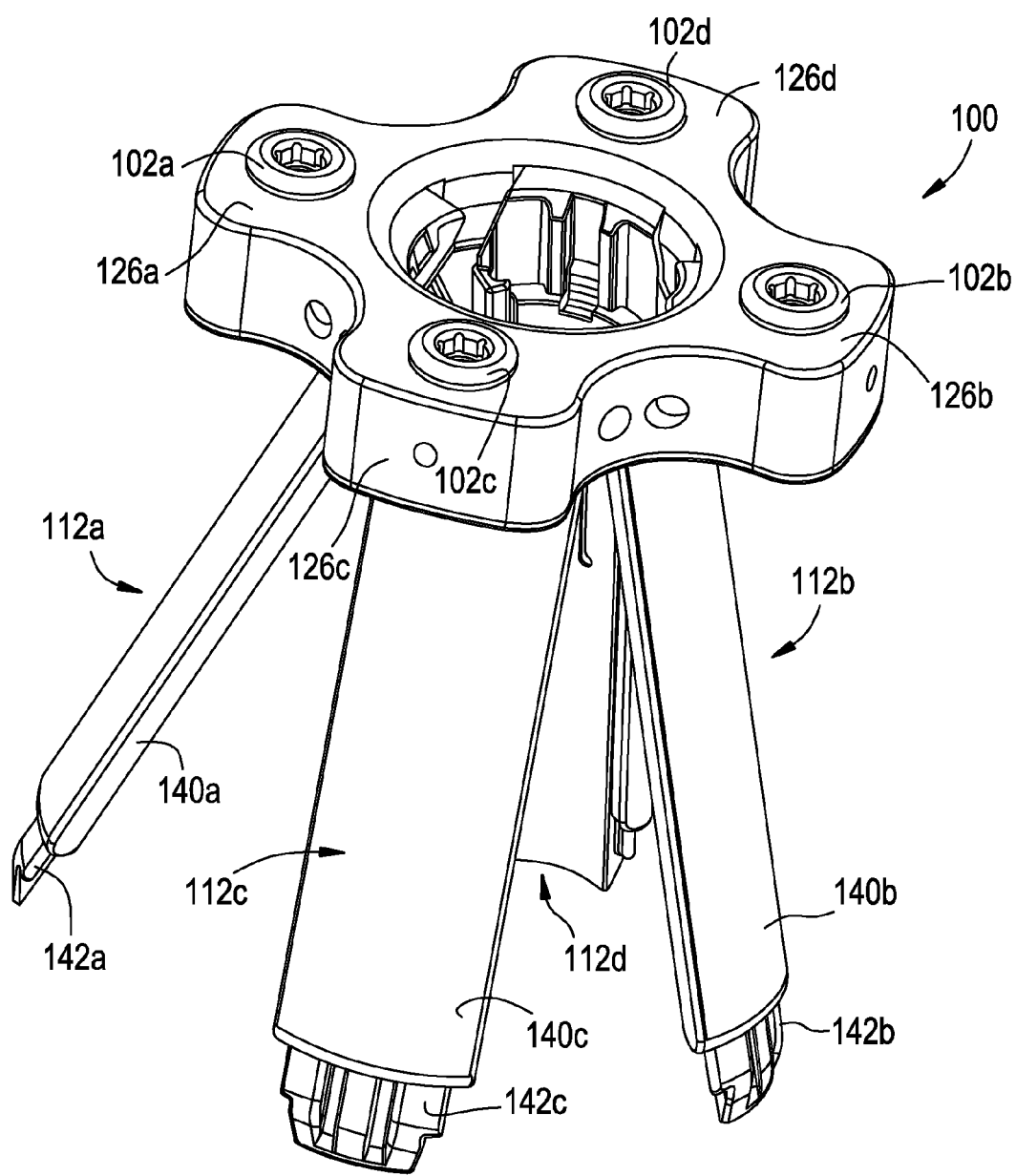
FIG. 7 is perspective view of the surgical access device of FIG. 6, illustrating the device in an expanded configuration.
Figure 8:
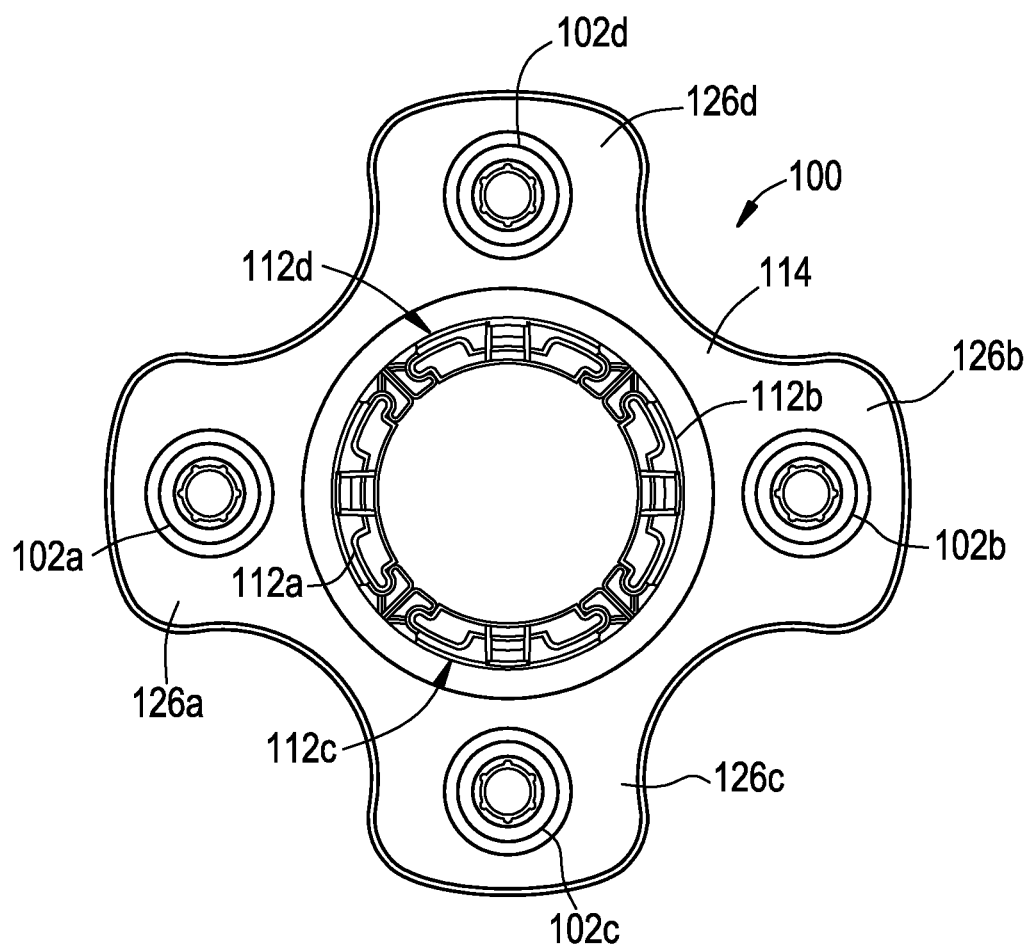
FIG. 8 is a top view of the surgical access device of FIG. 6.
Figure 9A:
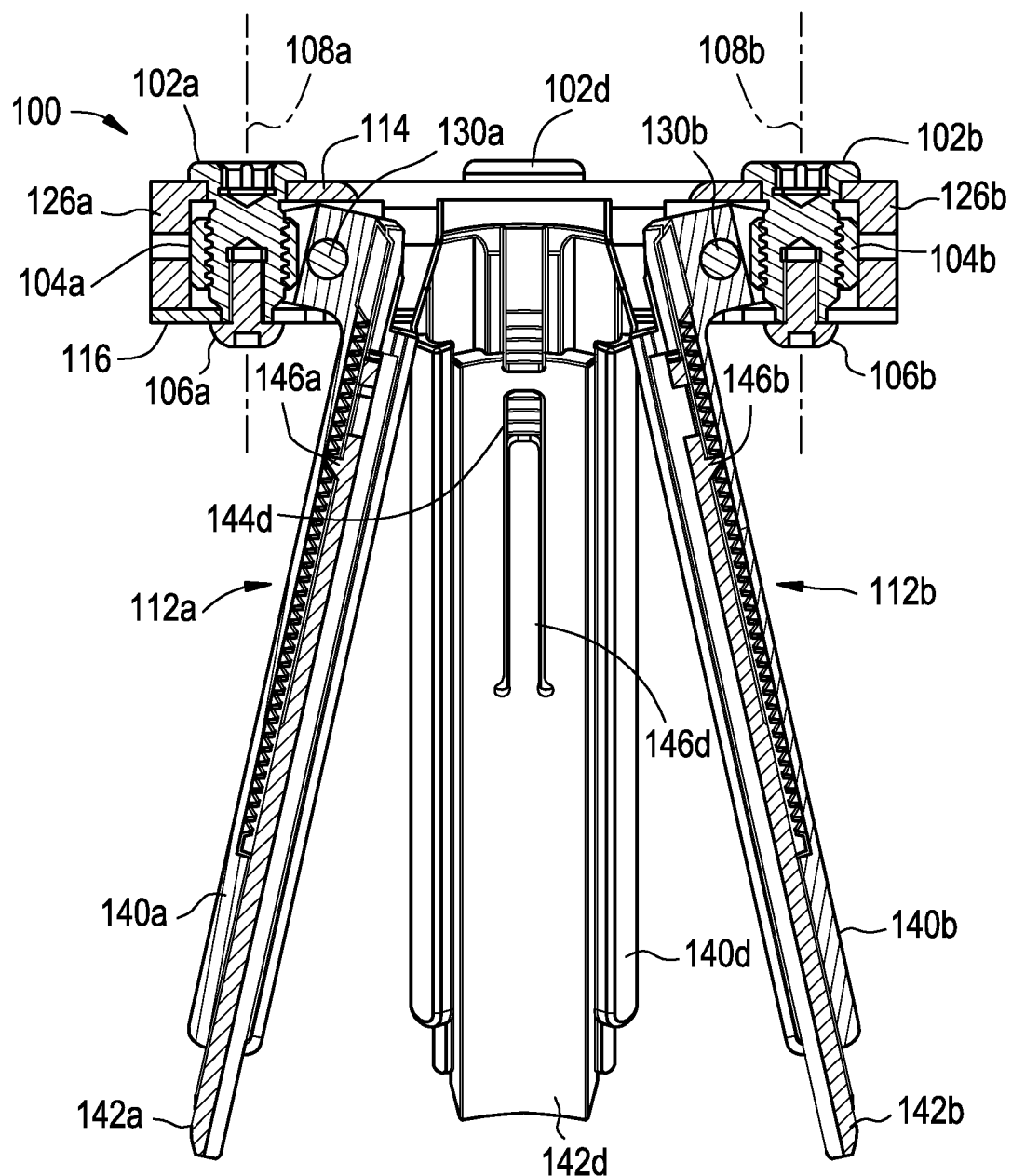
FIGS. 9A and 9B are side views in cross section (along different section lines) of the surgical access device of FIG. 6, illustrating the device in an expanded configuration (FIG. 9A) and in a closed configuration (FIG. 9B)
Figure 9B:
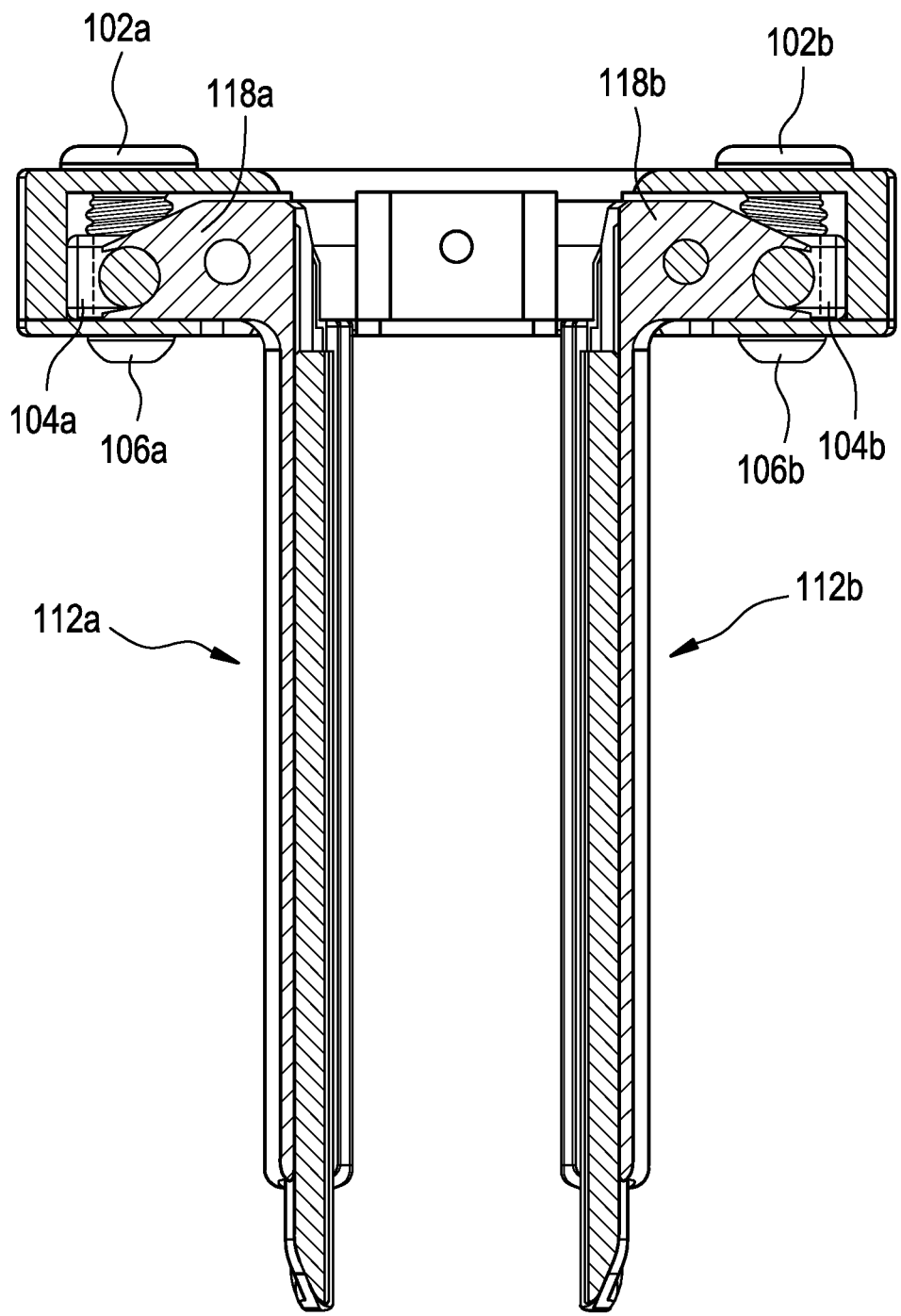

In use, each blade 12 may be rotated about a respective shaft 30 between a first, closed position in which the blade 12 is oriented approximately perpendicular the plane defined by the bottom surface 16 of the frame 14, as illustrated in FIGS. 1 and 4, and a second, fully expanded position in which a portion of the blade 12, for example, the distal end of the blade, is displaced a distance from a central axis 50 of the access channel 20, as illustrated in FIGS. 2 and 5. One or more of the blades 12 may be independently rotated to any position between the first, closed position and the second, fully expanded position to selectively expand the access channel 20. When each blade 12a-d is in the first, closed position, adjacent blades 12 are proximate to each other along the lateral edges of the blades 12 to form a continuously approximately enclosed access channel 20. In the exemplary embodiment, when each blade 12a-d is in the first, closed position, adjacent blades 12 contact each other along the lateral edges of the blades 12 to form a continuously fully enclosed access channel 20. The cross sectional size and shape of the access channel 20 in the closed configuration may vary depending on, for example, the number of blades provided, the surgical procedure being performed and the designed approach, e.g., anterior, lateral, or posterior. In the exemplary embodiment, the blades 12a-d form a cylindrical access channel 20 having a circular cross section when the blades 12a-d are in the first, closed position. The amount of rotational adjustment for the blades between the first, closed position and the second, fully expanded position may be varied. For example, in the exemplary embodiment, each blade 12 may rotate approximately 45° between the first, closed position and the second, fully expanded position.

The surgical access device 10 may include a blade adjustment mechanism for selectively adjusting the rotational position of a rotationally adjustable blade. In the illustrated exemplary embodiment, for example, the blade adjustment mechanism may be a pawl 60 pivotally connected to the frame 14 for selectively engaging a plurality of teeth 70 provided on the proximal end 18 of a blade 12. For example, each connection node 26a-d of the exemplary surgical access device 10 may include a pawl 60a-d pivotally connected thereto. In particular, referring to connection node 26b for example, the connection node 26b may include a shaft 62b positioned through openings 64b provided in the frame 14 and through an opening 66b in the pawl 60b. The pawl 60b may pivot about the shaft 62b into and out of engagement with the teeth 70b provided on the proximal end 18b of the second blade 12*b*. The pawl 60*b* may be biased into engagement with the teeth 70*b* of the second blade 12*b* by, for example, a spring 68*b*. The teeth 70*b* may be provided on an arcuate surface 72*b* of the proximal end 18*b* of the second blade 12*b* to facilitate rotational positioning of the second blade 12*b*. When the pawl 60*b* is engaged with the teeth 70*b* of the second blade 12*b*, the pawl 60*b* inhibits rotation of the second blade 12*b*. When the pawl 60*b* is pivoted out of engagement with the teeth 70*b*, the second blade 12*b* may be rotated into the desired rotational position.

In alternative embodiments, the blade adjustment mechanism may have a different structure. Referring to FIGS. 6-9B, for example, the blade adjustment mechanism of the exemplary surgical access device 100 may include a screw 102 received within an internally threaded bushing 104 positioned in a connection node 126 and connected to the proximal end 118 of a tissue engaging blade 112 of the surgical access device 100. Rotation of the screw 102 causes the bushing 104 to move along the axis of the screw 102 thereby adjusting the rotational position of a rotationally adjustable blade 112. In particular, referring to connection node 126*a* of the exemplary surgical access device 100 and to FIGS. 9A-B, a screw 102*a* is positioned through an opening in the top surface of the frame 114 and through the internally threaded bushing 104*a* positioned in the connection node 126*a*. The exemplary screw 102*a* is cannulated at the distal end of the screw 102*a*. A bolt 106*a* positioned through an opening in the bottom surface 116 of the frame 114 is positioned within the cannulated distal end of the screw 102*a* to inhibit movement of the screw 102*a* off of a screw axis 108*a* that is oriented approximately perpendicular to the plane defined by the bottom surface 116 of the frame 114. Rotation of the screw 102*a* in a first direction causes the first blade 112*a* to rotate about shaft 130*a* from a first, closed position, illustrated in FIG. 6 and FIG. 9B, toward a second, fully expanded position, illustrated in FIGS. 7 and 9A. Rotation of the screw 102*a* in a second direction, opposite the first direction, causes the first blade 112*a* to rotate about shaft 130*a* from an expanded position toward the closed position.

Figure 10:
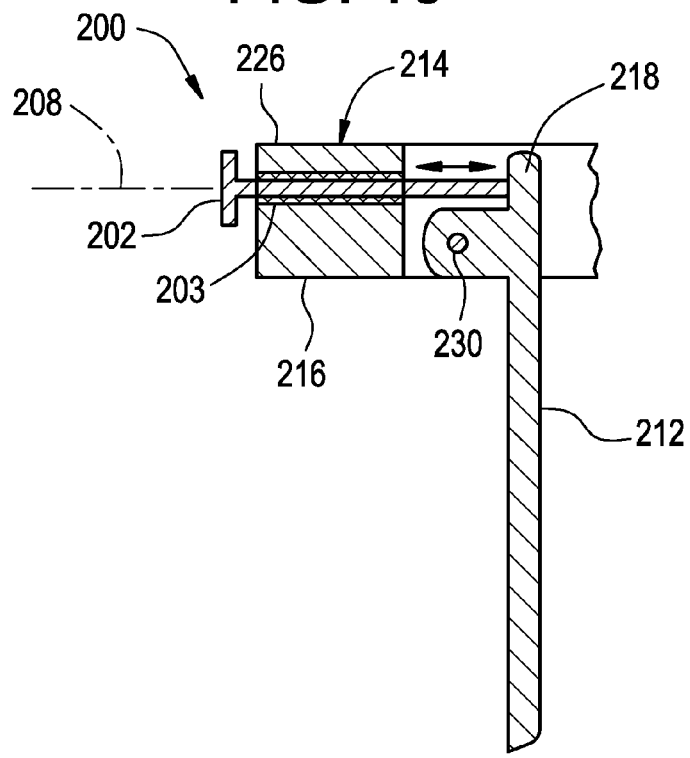
FIG. 10 is a partial side view in cross section of another alternative embodiment of a surgical access device, illustrating an exemplary connection node of the surgical access device.

Referring to FIG. 10, an exemplary embodiment of a surgical access device 200 having an alternative blade adjustment mechanism is illustrated. FIG. 10 illustrates an exemplary connection node 226 of the surgical access device 200. The blade adjustment mechanism of the exemplary surgical access device 200 includes a screw 202 received within a threaded hole 203 provided in the frame 214. The screw 202 has a screw axis 208 that is oriented generally parallel to the plane defined by the bottom surface 216 of the frame 214. The distal end of the screw 202 may engage the proximal end 218 of the tissue engaging blade 212. Movement of the screw 202 along a screw axis 208 relative to the frame 214 adjusts the rotational orientation of the first blade by rotating the blade 212 about shaft 230.

Figure 11:
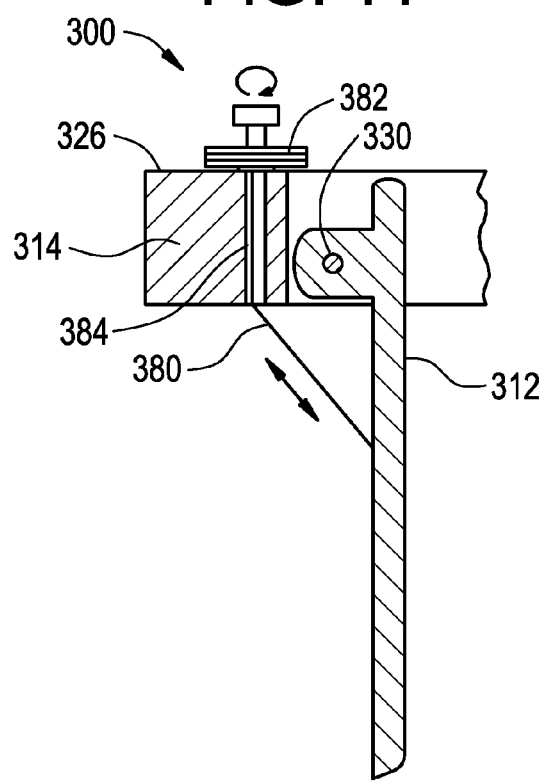
FIG. 11 is a partial side view in cross section of another alternative embodiment of a surgical access device, illustrating an exemplary connection node of the surgical access device

Referring to FIG. 11, an exemplary embodiment of a surgical access device 300 having an alternative blade adjustment mechanism is illustrated. FIG. 11 illustrates an exemplary connection node 326 of the surgical access device 300. The blade adjustment mechanism of the exemplary surgical access device 300 includes cable 380 positioned through an opening 384 in the frame 314 of the surgical access device 300. The cable 380 may be connected at one end to a tissue engaging blade 312. At the other end, the cable 380 may be connected to a wheel 382 about which the cable 380 may be wound. Rotation of the wheel 382 can cause the cable 380 to pull on the blade 312 and rotate the blade 312 about the shaft 330. A spring may be provided to bias the blade 312 to the first, closed position.

Figure 12:
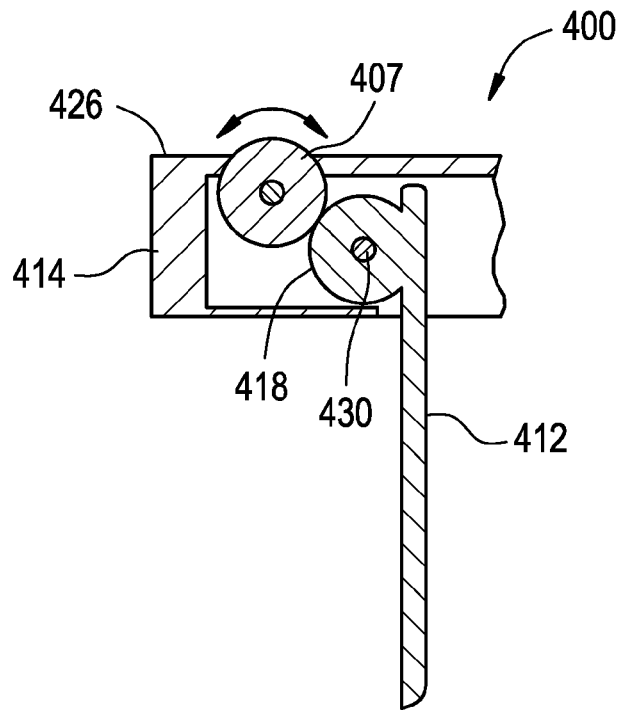
FIG. 12 is a partial side view in cross section of another alternative embodiment of a surgical access device, illustrating an exemplary connection node of the surgical access device.

Referring to FIG. 12, an exemplary embodiment of a surgical access device 400 having an alternative blade adjustment mechanism is illustrated. FIG. 12 illustrates an exemplary connection node 426 of the surgical access device 400. The blade adjustment mechanism of the exemplary surgical access device 400 includes a rotatable disk 407 rotatably connected to the connection node 426 and engageable with the proximal end 418 of the tissue engaging blade 412. In the exemplary embodiment, the proximal end 418 of the blade 412 includes an arcuate surface for engaging the disk 407. Rotation of the disk 407 relative to the frame 414 adjusts the rotational orientation of the blade 412 by rotating the blade 412 about shaft 430. In certain exemplary embodiments, the disk 407 may be a gear having teeth for engaging teeth provided on the arcuate surface of the proximal end 418 of the blade 412.

Figure 13:
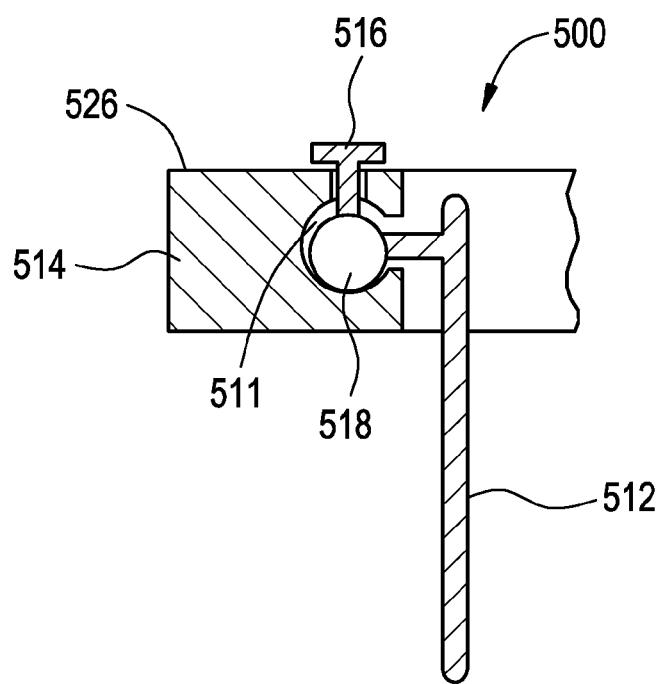
FIG. 13 is a partial side view in cross section of another alternative embodiment of a surgical access device, illustrating an exemplary connection node of the surgical access device.

Referring to FIG. 13, an exemplary embodiment of a surgical access device 500 having an alternative blade adjustment mechanism is illustrated. FIG. 13 illustrates an exemplary connection node 526 of the surgical access device 500. The blade adjustment mechanism of the exemplary surgical access device 500 includes a cavity 511 provided in the frame 514 for receiving the proximal end 518 of a tissue engaging blade 512. In the exemplary embodiment, the cavity 511 has a size and shape complementary to the size and shape of the proximal end 518 of the blade 512 and selected to allow the blade 512 to rotate relative to the frame 514. In the exemplary embodiment, for example, the proximal end 518 of the blade 512 may be approximately spherical in shape and the cavity 511 may include a seat that is approximately spherical in shape for engaging the proximal end 518 of the blade 512. A screw 513 or the like may be provided to fix the proximal end 518 of the blade 512 into contact with the seat of the cavity 511 and thereby inhibit rotation of the blade 512.

One skilled in the art will appreciate that other blade adjustment mechanisms may be employed to adjust the rotational position of a rotationally adjustable blade.

One or more of the blades of the surgical access device may have an adjustable length, e.g. the blade may telescope to selectively adjust the length of the blade. Referring to the exemplary embodiment illustration in FIGS. 6-9, for example, one or more of the blades 112 may include a primary blade 140 connected to the frame 114 and an adjustable blade 142 that is operatively coupled to the primary blade and is adjustable relative to the primary blade 140 along the length of the primary blade 140. In the exemplary embodiment, blades 112*a-d* are adjustable in length and include a respective primary blade 140*a-d* and a respective adjustable blade 142*a-d*. Exemplary tissue engaging blades having an adjustable length are disclosed in U.S. Patent Application Publication No. 2005-0137461 A1, which is incorporated herein by reference. The telescoping blades may include a mechanism for selectively adjusting the position of the adjustable blade 142 relative to the primary blade 140. For example, the primary blade 140 may include a plurality of teeth 144 extending along the longitudinal axis of the primary blade 140 and the adjustable blade 142 may include a flexible tab 146 for engaging the teeth 144 of the primary blade 140. The surgical access device may be inserted through an incision with the adjustable blades 142 in place, as in the case of the exemplary surgical access device 100 illustrated in FIGS. 6-9. Alternatively, the surgical access device may be inserted through an incision without the adjustable blades in place, as in the case of the exemplary surgical access device 10 illustrated in FIGS. 1-5. In such embodiments, the surgical access device 10 may be inserted with the primary blades 40*a-d* and one or more adjustable blades may be added after insertion.

The components of the surgical access devices disclosed herein may be manufactured from any biocompatible material including metals, such as stainless steel or titanium, polymers, or composite materials. The components, such as the blades and the frame, may be constructed from the same or different materials.

An exemplary method of providing minimally invasive access to spinal anatomy employing a surgical access device disclosed herein may include making a skin incision for insertion of the surgical access device. The incision initially may be less than the diameter of the surgical access device in the closed configuration (e.g., with the blades of the device in the first, closed position). The incision may be expanded to accommodate the surgical access device by dilation, for example, by placing one or more dilators through the incision to expand the incision in a stepwise manner. The dilators may be employed to separate or dissect the underlying tissue to the target spinal anatomy. Alternatively, the surgeon may employ his finger or the surgical access device to dissect the underlying tissue and to expand the initial incision.

The blades of a surgical access device may be inserted through the incision and the distal ends of the blades may be advanced into proximity to the spinal anatomy. The blades are preferably advanced in the first, closed position, in which the blades are proximate to each other to form a continuously approximately enclosed access channel between the frame, which located at the surface of the skin, and the distal ends of the blades. One or more of the blades may be rotated, using a blade adjustment mechanism, independent of the other blade to selectively expand the access channel. In the case of the exemplary surgical access device 10 and the exemplary surgical access device 100, rotational adjustment of some or all of the blades of the device expands the access channel, particularly at the distal end of the access channel, thereby creating greater working space at proximate the target spinal anatomy. In addition, the length of the working channel may be increased by advancing an adjustable blade of one of the plurality of blades relative to a primary blade along a longitudinal axis of the primary blade.

Any number of surgical procedures may be performed through the access channel including, for example, removal of some or all of one or more discs, placement of bone fusion promoting material, placement of any spine arthroplasty device such as an artificial disc, placement of spinal implants such as hooks, rods, and screws.

After the surgical procedure is performed, the surgical access device may be returned to the closed configuration and removed from the incision.

While the devices and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. A surgical access device comprising:
a proximal frame of fixed construction, the proximal frame defining a housing, the housing having a planar bottom surface defining a first plane, a top surface spaced apart from the bottom surface, an inner surface connecting the top surface and the bottom surface, and an outer surface spaced apart from the inner surface, the inner surface including a plurality of spaced apart openings to the housing, the housing including a central opening through the top surface and the bottom surface;
a plurality of tissue engaging blades, each blade having a proximal end and a distal end, the proximal end of each blade including an opening, the proximal end of each blade including the opening positioned within the housing, each blade positioned within one of the spaced apart openings in the inner surface and extending from the frame such that the distal end of each blade is positioned outside of the housing of the frame, the plurality of blades and the inner surface aligned to enclose and define the central opening in the housing; and
a plurality of blade adjustment mechanisms spaced about the frame, each blade adjustment mechanism comprising a shaft positioned through the opening in the proximal end of one of the blades such that each blade is rotatable about its respective shaft, each shaft defining a rotation axis for a respective blade, each blade adjustment mechanism further comprising a screw received within a threaded bushing connected to one of the blades, rotation of the screw causing the bushing to move along an axis of the screw to adjust the rotational orientation of the blade independent of other blades.

2. The surgical access device of claim 1, wherein at least one of the plurality of tissue engaging blades comprises a primary blade connected to the proximal frame, and an adjustable blade operatively coupled to the primary blade and adjustable relative to the primary blade along a longitudinal axis of the primary blade.

3. The surgical access device of claim 2, wherein the primary blade includes a plurality of teeth extending along the longitudinal axis of the primary blade and the adjustable blade includes a flexible tab for engaging the teeth of the primary blade.

4. The surgical access device of claim 1, wherein the shafts and the respective rotation axes of each blade adjustment mechanism are positioned in a common plane that is parallel to the first plane.

5. The surgical access device of claim 4, wherein the shafts and the respective rotation axes of each blade adjustment mechanism are positioned within the housing between the top surface and the bottom surface.

6. The surgical access device of claim 1, wherein the shafts and the respective rotation axes of each blade adjustment mechanism are positioned within the housing between the top surface and the bottom surface.

7. The surgical access device of claim 1, wherein the screw axis is oriented approximately perpendicular to the first plane.

8. The surgical access device of claim 1, wherein the plurality of the blades are rotatable between a closed position in which the distal end of each blade is oriented perpendicular to the first plane and an open position in which one or more of the blades is orientated at an angle other than 90 degrees relative to the first plane.

9. The surgical access device of claim 8, wherein when the blades are in the closed position each blade contacts an adjacent blade along a lateral edge to form a continuous fully enclosed access channel.

10. A surgical access device comprising:
a proximal frame of fixed construction, the proximal frame defining a housing, the housing having a planar bottom surface defining a first plane, the bottom surface including four equally spaced apart openings to the housing;
a first blade having a proximal end and a distal end, the proximal end of the first blade including an opening, the proximal end of the first blade including the opening being positioned within the housing, the first blade extending through a first one of the spaced apart openings in the frame such that the distal end of the first blade is positioned outside of the housing of the frame;

a first blade adjustment mechanism including a first shaft positioned through the opening in the proximal end of the first blade such that the first blade is rotatable about the first shaft, the first blade adjustment mechanism further comprising a first screw received within a threaded first bushing connected to the first blade, rotation of the first screw causing the first bushing to move along an axis of the first screw to adjust the rotational orientation of the first blade about the first shaft and independent of other blades;

a second blade having a proximal end and a distal end, the proximal end of the second blade including an opening, the proximal end of the second blade including the opening being positioned within the housing, the second blade extending through a second one of the spaced apart openings in the frame such that the distal end of the second blade is positioned outside of the housing of the frame;

a second blade adjustment mechanism including a second shaft positioned through the opening in the proximal end of the second blade such that the second blade is rotatable about the second shaft, the second blade adjustment mechanism further comprising a second screw received within a threaded first bushing connected to the first blade, rotation of the first screw causing the second bushing to move along an axis of the second screw to adjust the rotational orientation of the second blade about the second shaft and independent of other blades;

a third blade having a proximal end and a distal end, the proximal end of the third blade including an opening, the proximal end of the third blade including the opening being positioned within the housing, the third blade extending through a third one of the spaced apart openings in the frame such that the distal end of the third blade is positioned outside of the housing of the frame;

a third blade adjustment mechanism including a third shaft positioned through the opening in the proximal end of the third blade such that the third blade is rotatable about the third shaft, the third blade adjustment mechanism further comprising a third screw received within a threaded third bushing connected to the third blade, rotation of the third screw causing the third bushing to move along an axis of the third screw to adjust the rotational orientation of the third blade about the third shaft and independent of other blades;

a fourth blade having a proximal end and a distal end, the proximal end of the fourth blade including an opening, the proximal end of the fourth blade including the opening being positioned within the housing, the fourth blade extending through a fourth one of the spaced apart openings in the frame such that the distal end of the fourth blade is positioned outside of the housing of the frame; and a fourth blade adjustment mechanism including a fourth shaft positioned through the opening in the proximal end of the fourth blade such that the fourth blade is rotatable about the fourth shaft, the fourth blade adjustment mechanism further comprising a fourth screw received within a threaded fourth bushing connected to the fourth blade, rotation of the fourth screw causing the fourth bushing to move along an axis of the fourth screw to adjust the rotational orientation of the fourth blade about the fourth shaft and independent of other blades.

11. The surgical access device of claim 10, wherein first, second, third, and fourth blades each comprise a primary blade connected to the proximal frame, and an adjustable blade operatively coupled to the primary blade and adjustable relative to the primary blade along a longitudinal axis of the primary blade.

12. The surgical access device of claim 10, wherein the first, second, third, and fourth blades are rotatable between a closed position in which the distal end of each blade is oriented perpendicular to the first plane and an open position in which one or more of the blades is orientated at an angle other than 90 degrees relative to the first plane.

13. The surgical access device of claim 12, wherein when the blades are in the closed position each blade contacts an adjacent blade along a lateral edge to form a continuous fully enclosed access channel.

* * * * *